US006638562B1

(12) United States Patent
Saitoh et al.

(10) Patent No.: US 6,638,562 B1
(45) Date of Patent: Oct. 28, 2003

(54) FRACTIONATION OF SOYBEAN 7S GLOBULIN AND 11S GLOBULIN AND PROCESS FOR PRODUCING THE SAME

(75) Inventors: Tsutomu Saitoh, Tsukuba-gun (JP); Kazunobu Tsumura, Tsukuba-gun (JP); Wataru Kugimiya, Tsukuba-gun (JP); Mitsutaka Kohno, Tsukuba-gun (JP)

(73) Assignee: Fuji Oil Company Limited, Osaka-fu (JP)

( * ) Notice: Subject to any disclaimer, the term of this patent is extended or adjusted under 35 U.S.C. 154(b) by 0 days.

(21) Appl. No.: 09/914,260

(22) PCT Filed: Mar. 30, 2000

(86) PCT No.: PCT/JP00/02051

§ 371 (c)(1),
(2), (4) Date: Aug. 24, 2001

(87) PCT Pub. No.: WO00/58492

PCT Pub. Date: Oct. 5, 2000

(30) Foreign Application Priority Data

Mar. 30, 1999 (JP) ............................................. 11-089834

(51) Int. Cl.⁷ ................................................. A23L 1/20
(52) U.S. Cl. ....................................................... 426/654
(58) Field of Search ................................. 426/654, 656, 426/634, 46; 435/68.1

(56) References Cited

U.S. PATENT DOCUMENTS

| | | | |
|---|---|---|---|
| 3,733,207 A | | 5/1973 | McCabe |
| 4,370,267 A | | 1/1983 | Lehnhardt et al. |
| 4,771,126 A | | 9/1988 | Hirotsuka et al. |
| 6,303,178 B1 | * | 10/2001 | Tsumura et al. ............. 426/654 |

FOREIGN PATENT DOCUMENTS

| | | |
|---|---|---|
| EP | 0 666 034 | 8/1985 |
| WO | 90/8476 | 8/1990 |

* cited by examiner

*Primary Examiner*—Karen Cochrane Carlson
*Assistant Examiner*—Sheridan K Snedden
(74) *Attorney, Agent, or Firm*—Wenderoth, Lind & Ponack, L.L.P.

(57) ABSTRACT

A method for fractionation of soybean protein into a 7S globulin-rich fraction and an 11S globulin-rich fraction which comprises treating a soybean protein-containing solution with an enzyme or an enzyme preparation having an activity of decomposing phytic acid to thereby separate into a soluble fraction and an insoluble fraction at a specific pH value.

7 Claims, 1 Drawing Sheet

Figure 1:
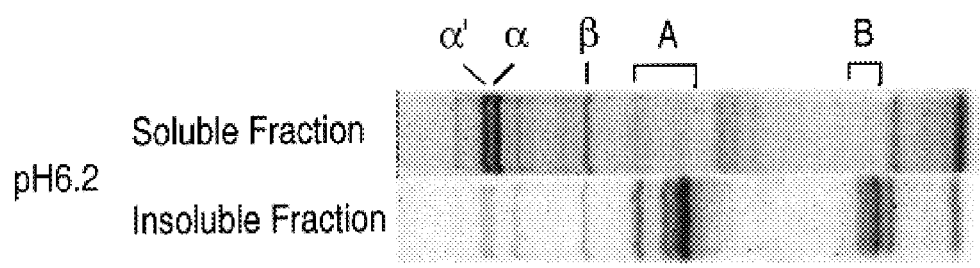

FRACTIONATION OF SOYBEAN 7S GLOBULIN AND 11S GLOBULIN AND PROCESS FOR PRODUCING THE SAME

This application is a 371 of PCT/JP00/02051 filed Mar. 30, 2000, which claims priority to Japan 898,34/1999 filed Mar. 30, 1999.

FIELD OF THE INVENTION

The present invention relates to a method for fractionating and a process for producing a 7S globulin-rich fraction and an 11S globulin-rich fraction from a soybean protein-containing solution.

BACKGROUND ART

Soybean storage protein is precipitated at about pH 4.5 and can be relatively easily separated from components other than the protein. This is referred to as isolated soybean protein and, in many cases, soybean protein in this form is utilized in the food industry. The protein is further divided into 2S, 7S, 11S and 15S globulins according to sedimentation constants in ultracentrifugation analysis. Among them, 7S globulin and 11S globulin are predominant constituent protein components of the globulin fractions (note: 7S globulin and 11S globulin are classification names in a sedimentation method and substantially correspond to β-conglycinin and glycinin according to immunological nomenclature, respectively), and both of them have specific different properties such as viscosity, coagulability, surface activity, etc. Then, factionation of 7S globulin and 11S globulin makes it possible to utilize properties of respective protein components, and it is expected to expand industrial utilization of proteins.

7S Globulin and 11S globulin are composed of several subunits. 7S Globulin is composed of three subunits, i.e., α, α' and β subunits. 11S Globulin is composed of several subunits each of which is a pair of an acidic polypeptide (A) and a basic polypeptide (B). The molecular weights and charge states of 7S globulin and 11S globulin are very similar to each other. In particular, both globulins are diversified due to combinations of subunits, and properties thereof range to some extent to thereby overlap each other. Then, for fractionating both globulins effectively, a certain essential difference should be found out.

Known fractionation methods are as follows. That is, a method utilizing a difference in isoelectric point: extraction is carried out by adjusting pH to about the isoelectric point of 11S globulin and only 7S globulin is extracted (JP 55-124457 A); a method utilizing a difference in reactivity with calcium: a small a-mount of a calcium salt is added upon extraction to extract a 7S globulin-rich fraction (JP 48-56843 A); a method utilizing a difference in solubility at a certain pH and ionic strength: an insoluble fraction is removed in the presence of sodium chloride or potassium chloride at pH 1.2 to 4.0 to prepare 7S protein (JP 49-31843 A), or a slurry precipitated at an isoelectric point is adjusted to pH 5.0 to 5.6 and its molar concentration of sodium chloride is adjusted to 0.01 to 2 M to separate 7S and 11S fractions (JP 58-36345 A); and a method utilizing a cold-precipitation phenomenon and a reducing agent, etc.: this utilizes a phenomenon that the solubility of 11S globulin is lowered at a low temperature (referred to as cryo-precipitation phenomenon), and a soybean protein raw material is treated in the presence of a sulfurous acid compound, glutathione compound or cysteine compound in an aqueous system at pH 6.5 or higher, followed by adjusting pH to 5.5 to 7.0 and a temperature to 20° C. or lower to fractionate into a 7S globulin-rich fraction and an 11S globulin-rich fraction (JP 61-187755 A).

These known fractionation methods skillfully utilize a difference in solubility between 7S globulin and 11S globulin due to pH, ionic strength, the presence of a certain salt, temperature, etc. However, there are such problems that these known fractionation methods are unsuitable for an industrially applicable fractionation method because clear fractionation of both globulins cannot be achieved due to overlap of their properties as mentioned above or, even if clear fractionation can be achieved to some extent, these methods are still those for the level of experimental use. Thus, problems still remain in practice. For example, in the method of JP 61-187755 A, cryo-precipitation phenomenon highly depends on a temperature and it is necessary to cool a reaction mixture to about 5° C., which results in such a practical problem that a large amount of a sulfurous acid compound, etc. should be added to separate fractions with an industrially available low centrifugal force, as well as which results in such a problem of fractionation precision that a little amount of 11S globulin is contaminated in a soluble fraction.

Then, it has been desired to develop a fractionation method which can simply and efficiently produce a 7S globulin-rich fraction and an 11S globulin-rich fraction in an industrial scale with minimizing contamination of the soluble fraction with the insoluble fraction or vice versa.

On the other hand, phytic acid is an organic phosphate compound (myo-inositol hexakis-phosphate: 6 phosphoric acid groups are attached to inositol) which is predominantly present in plant seeds in the form of its calcium salt, magnesium salt and potassium salt. Soybeans contain about 1% of phosphorus most of which is present in the form of phytin. Since phytic acid forms a slightly soluble compound by being attached to a nutritiously important mineral component (calcium, magnesium, iron, zinc, etc.) through a chelate bond, it is pointed out that phytic acid lowers absorption of these trace minerals in a living body. In addition, phytic acid tends to form a complex with a protein and a multivalent metal cation and, normally, soybean protein contains 1 to 3% by weight of phytic acid based on the weight of the protein. An activity of decomposing phytic acid used herein refers to the activity for liberating phosphoric acid from phytic acid. A representative enzyme having such an activity is phytase.

Utilization of phytase which has an activity of decomposing phytic acid of soybean protein is divided into that for removing phytic acid which is considered to be an inhibitor of mineral absorption and that for recovering a protein having a high solubility under acidic conditions (pH 5 or lower). Examples of the former include those described in JP 49-7300 A, JP 50-130800 A and JP 4-503002 A. Examples of the latter include a method for isolating a soluble protein fraction from a phytic acid-containing protein material which comprises adding phytase to an aqueous suspension of a phytin-containing soybean protein material to decompose phytin, adjusting the suspension to pH about 4.6 to form an insoluble precipitate, collecting a protein solution, adjusting the protein solution to pH about 5.0 to 5.4 to precipitate a protein fraction and collecting the precipitated protein fraction (JP 48-18450 A); and a method for collecting a protein from a vegetable protein raw material which comprises washing the vegetable protein raw material with water at an isoelectric point, digesting the washed vegetable protein raw material with acidic phytase, and separating a soluble protein-containing liquid extract from an insoluble digested residue to collect the protein (JP 51-125300 A).

Phytase is reacted under the following conditions (extracted from Examples of each publication). JP 49-7300 A: endogenous phytase, pH 5, 65° C., 9.3 hours; JP 50-130800 A: wheat phytase, pH 5.5, 45° C., 16 hours; JP 4-503002 A: microorganism phytase, pH 5.0, 40° C., 4 hours; JP 48-18450 A: wheat phytase, pH 6, 50–55° C., 24 hours; and JP 51-125300 A: microorganism phytase, pH 2.8, 50° C., 10 hours.

Since bacteria generally tend to grow at pH 5 or higher, normally, a solution containing soybean protein is liable to be putrefied unless it is subjected to sterilization treatment such as heat sterilization, etc. In addition, since a protein is liable to be denatured with an acid by treatment under strong acidic conditions such as at pH 2.8 for a long period of time, such treatment adversely affects fractionation of 7S globulin and 11S globulin. Further, in the method of JP 51-125300 A, the dissolved fraction is fractionated from "okara (insoluble residue from soybean milk or tofu production)" component after treatment with phytase. Therefore, this does not teach acceleration of fractionation of 7S globulin and 11S globulin.

OBJECTS OF THE INVENTION

An object of the present invention is to propose a novel fractionation method and a production process of 7S globulin and 11S globulin, wherein an enzyme is utilized. Another object of the present invention is to provide a fractionation method having high fractionation precision with minimizing a contamination rate of respective fractions, which can be simply and efficiently carried out the production of both fractions in an industrial scale.

SUMMARY OF THE INVENTION

As a result of the present inventors' intensive study, the following have been found.

It has been found that fractionation capability of 7S globulin and 11S globulin is improved by treatment with phytase, which is an enzyme having an activity of decomposing phytic acid, at a certain pH. Further, it has also been found that, when a soybean protein-containing solution is treated with an enzyme or an enzyme preparation having an activity of decomposing phytic acid to decompose phytic acid and phytates contained therein, followed by separating them at an appropriate pH range, a 7S-rich fraction can be simply and readily passed into a soluble fraction, while passing an 11S-rich fraction into an insoluble fraction without overlapping to each other at room temperature without addition of a reducing agent, etc. Thus the present invention has been completed. Although the mechanism of this phenomenon is not fully elucidated, it is considered that phytic acid and phytates, which form a complex with a protein and a multivalent metal ion, are decomposed by treatment with phytase to cause change in solubility behavior of 7S globulin and 11S globulin, thereby increasing a difference in their solubility at a specific pH, which make their fractionation possible.

The present invention is a method for fractionation or a process for producing a 7S globulin-rich fraction and an 11S globulin-rich fraction which comprises treating a soybean protein-containing solution with an enzyme or an enzyme preparation having an activity of decomposing phytic acid and separating it into a soluble fraction and an insoluble fraction at a specific pH.

DETAILED DESCRIPTION OF THE INVENTION

Hereinafter, preferred embodiments of the present invention will be described. Soybean protein used in the present invention is preferably that from which insoluble residue ("okara") has been removed. Examples thereof include soybean protein such as soybean milk (including dried soybean milk powder), isolated soybean protein and the like, whose protein is native or with little denaturation, that is, soybean protein which is processed lightly without denaturation, or with minimizing denaturation. In general, defatted-soybeans obtained by extraction with n-hexane at a low temperature are suitable for a starting material. In particular, defatted-soybeans, which are scarcely denatured and have the nitrogen solubility index (NSI) of 60 or more, preferably 80 or more, are preferred. Preferably, defatted-soybean milk and isolated soybean protein obtained from such scarcely denatured defatted-soybeans are used in the present invention.

In addition, it is preferred to avoid protein denaturation due to heating and severe conditions (e.g., strong acidic or strong alkaline conditions, etc.) as much as possible during production steps (e.g., extraction step, step for adjusting pH, etc.) thereof. Preferably, a heat sterilization step is also avoided. Normally, the phytic acid content of a solution containing thus-obtained soybean protein without denaturation or with little denaturation is 1 to 3% by weight based on the weight of the protein.

Whether protein in a soybean protein-containing solution is denatured with heat, etc. or not can be judged by analysis of the protein with Differential Scanning Calorimetry (DSC) (Nagano et al., J. Agric. Food Chem., 40, 941–944 (1992)). According to this analysis, for example, respective endothermic peaks derived from its main constituent components, 7S and 11S globulins, can be recognized in case of isolated soybean protein which is not denatured. However, when isolated soybean protein undergoes excess denaturation, no endothermic peak derived from the constituent components is observed. Therefore, presence or absence of denaturation can be readily judged.

The enzyme or the enzyme preparation having an activity of decomposing phytic acid to be used in the present invention is not specifically limited and there can be used enzymes such as phytase, phosphatase, etc. which have an activity of decomposing phytic acid and derived from vegetables such as wheat, potato, etc.; animal organs such as the intestinal tracts, etc.; and microorganisms such as bacteria, yeast, mold, actinomycetes, etc. Preferably, the enzyme or the enzyme preparation to be used has no or less protease activity because the protease activity causes not only interference with fractionation of 7S globulin and 11S globulin due to hydrolysis thereof to change their solubility behavior, but also difficulties in recovery of 7S globulin and 11S globulin as proteins. For example, in case that there is no or less protein hydrolysis with the protease activity, a TCA solubilization degree of soybean protein after treatment of the enzyme or the enzyme preparation can be defined as 20% or less, preferably 15% or less. The term "TCA solubilization degree" used herein is a ratio of the protein solubilized with 0.22 M trichloroacetic acid (TCA) to the total protein measured by a protein determination method such as Kjeldahl method, Lowry method, etc. In general, an activity of decomposing of phytic acid of the enzyme or the enzyme preparation derived from bacteria is higher than that derived from vegetables, and the protease activity of the former is lower than the latter. Therefore, the former is advantageous in view of prevention of hydrolysis and putrefaction of protein.

For practicing the present invention, it is necessary to treat a soybean protein-containing solution with the enzyme or the enzyme preparation having an activity of decomposing phytic acid to decomposed phytic acid and phytates contained therein in order to fractionate into a 7S globulin-rich fraction and an 11S globulin-rich fraction.

Although the degree of decomposition of phytic acid and phytates is not specifically limited, for example, preferably, phytic acid content is reduced by 50% or more in comparison with that before treatment with the enzyme or the enzyme preparation. Therefore, the conditions of treatment with the enzyme or the enzyme preparation are not specifically limited in so far as the above conditions are satisfied and optimal conditions of each enzyme or enzyme preparation can be employed. Further, a treatment method is not specifically limited. However, in order to avoid denaturation of protein due to treatment under severe conditions and putrefaction due to treatment for a long period of time, treatment time is preferably 5 minutes to 3 hours. When a certain measure for avoiding denaturation and putrefaction of protein is employed, treatment can also be carried out under conditions other than the above. For example, defatted-soybean with little denaturation is extracted with water and separated into a water insoluble fraction ("okara") and a water soluble fraction (soybean milk), and the water soluble fraction is subjected to decomposition of phytic acid at pH 3.5 to 9.0 and at a temperature of 20 to 70° C. The enzyme or the enzyme preparation having an activity of decomposing phytic acid may be added to the water soluble fraction after adjusting pH of the fraction to 3.5 to 9.0. The amount of the enzyme or the enzyme preparation to be added ranges 0.1 to 100 unit/g, preferably 0.5 to 50 unit/g and, normally, treatment is continued for 5 minutes to 3 hours. Where treatment for a shorter period of time is desired, treatment can be carried out with the enzyme or the enzyme preparation having a higher unit. One unit of phytase activity used herein is expressed by the amount of the enzyme which can liberate 1 μmol of phosphoric acid from the substrate, phytic acid, during 1 minute in an initial stage of the reaction under conditions at pH 5.5 and at 37° C.

The degree of decomposition of phytic acid and phytates used herein was determined by measuring the amount of phytic acid in the solution directly. The amount of phytic acid was measured according to the method of Alii Mohamed (Cereal Chemistry, 63, 475, 1980).

When the soybean protein-containing solution after treatment of the enzyme or the enzyme preparation having an activity of decomposing phytic acid is adjusted to pH 5.6 to 6.6, preferably, pH 5.8 to 6.4, a 7S globulin-rich fraction and an 11S globulin-rich fraction can be readily separated. Since this process can be carried out regardless of separation temperature and addition of a reducing agent, separation can be carried out without a cooling step (cold precipitation) and addition of a sulfurous acid compound, glutathione compound or cysteine compound as described in JP 61-187755 A, and this is therefore an industrially effective process. However, contamination of an insoluble fraction with 7S globulin increases when pH is <5.6, or contamination of a soluble fraction with 11S globulin increases when pH is >6.6. Then, no desired fractionation is expected. Preferably, when a soybean protein-containing solution is treated with the enzyme or the enzyme preparation at pH 5.6 to 6.6, more preferably pH 5.8 to 6.4, separation can be carried out more efficiently because re-adjustment of pH is not required.

Separation can be readily carried out by a known separation means (e.g., filtration, centrifugation, etc.), in particular, a continuous centrifugal separator (e.g., decanter) or the like. Of course, a non-continuous centrifugal separator such as a batch-wise one can also be used.

The state of fractionation of the 7S globulin-rich fraction and the 11S globulin-rich fraction according to the present invention can be evaluated based on a pattern obtained by SDS-polyacrylamide gel electrophoresis. In addition, for numerical expression of the amounts of 7S globulin and 11S globulin present in the insoluble and soluble fractions, respectively, their amounts were calculated based on the recovery rates of proteins in the insoluble and soluble fractions and the ratio of areas obtained by densitometry of the pattern obtained by SDS-polyacrylamide gel electrophoresis. 7S Globulin referred to herein is the total amount of α, α' and β subunits and the 11S globulin content is the total amount of the acidic polypeptide (A) and the basic polypeptide (B).

After separation, the soluble fraction and the insoluble fraction can be used as such, or can further be subjected to concentration, neutralization, or drying to use as a 7S globulin-rich fraction and an 11S globulin-rich fraction. For concentration, preferably, a precipitated curd is separated and recovered by isoelectric point precipitation of the soluble fraction (pH 4.5–5.3, preferably pH 4.7–5.1) from the viewpoint of improvement of physical properties. Further, after isoelectric point precipitation, the curd can also be subjected to neutralization, heat sterilization treatment or, further, treatment with an enzyme such as a protease, etc. a sterilized, powdered form is a most common product form. Heat sterilization treatment can also be carried out by known HTST treatment, UHT treatment and the like.

The following Examples specifically illustrate embodiments of the present invention, but are not to be construed to limit the scope thereof.

EXAMPLE 1

To scarcely denatured defatted-soybeans (1 part by weight) (NSI 91), which was obtained by flaking soybeans and extracting their oil with an extraction solvent, n-hexane, to separate and remove the oil, was added water (7 parts by weight). The mixture was extracted at pH 7 at room temperature for 1 hour, and then centrifuged to obtain defatted-soybean milk. The soybean milk was adjusted to pH 6.2 with hydrochloric acid and warmed to 40° C. To this solution (phytic acid content: 2.20%/weight of protein; TCA solubilization degree: 8.6%) was added phytase ("PHYTASE NOVO L" manufactured by NOVO) in an amount corresponding to 8 units per the weight of protein and enzyme treatment was carried out for 30 minutes. After the reaction, the mixture treated with the enzyme (phytic acid content: 0.05%/weight of protein; TCA solubilization degree: substantially the same as that before the reaction) was centrifuged without changing pH at 6.2 by a batch-wise centrifugal separator (2,000 G) to obtain an insoluble fraction and a soluble fraction. At this time, the insoluble fraction and the soluble fraction were clearly separated. The temperature of the mixture during centrifugation was about 30° C. To the insoluble fraction was added water (2 parts by weight) and the mixture was neutralized with sodium hydroxide. On the other hand, the soluble fraction was adjusted to pH 4.8 with hydrochloric acid and whey fraction was removed by centrifugation to obtain a precipitated curd. To the precipitated curd was added water (2 parts by weight) and the mixture was neutralized with sodium hydroxide. The respective neutralized fractions were sterilized at 140° C. for 15 seconds, and spray-dried to obtain two fractionated soybean proteins.

FIG. 1 shows a pattern of SDS-polyacrylamide gel electrophoresis of the insoluble and soluble fraction of Example 1.

For numerical expression of the amounts of 7S globulin and 11S globulin present in the above-separated insoluble and soluble fractions, respectively, their amounts were calculated based on the recovery rates of proteins in the insoluble and soluble fractions and the ratio of areas obtained by densitometry of the pattern obtained by SDS-polyacrylamide gel electrophoresis. The results are shown in Table 1.

TABLE 1

|  | Soluble fraction | Insoluble fraction |
|---|---|---|
| Protein | 55.2 | 44.8 |
| 7S | 26.3 | 3.0 |
| 11S | 1.0 | 34.9 |
|  | Contamination rate of 11S | Contamination rate of 7S |
| Contamination rate | 1.8% | 6.7% |

The values in Table 1 was calculated by taking the total amount of protein before centrifugation as 100.

Contamination rate of soluble fraction=Amount of 11S in soluble fraction/Amount of protein in soluble fraction Contamination rate of insoluble fraction=Amount of 7S in insoluble fraction/Amount of protein in insoluble fraction (Hereafter, the values in Tables were calculated according to the same way.)

Comparative Example 1

Defatted-soybean milk extracted by the same manner as that in Example 1 was adjusted to pH 6.2 with hydrochloric acid and then centrifuged with a batch-wise centrifugal separator (2,000 G). However, an insoluble fraction and a soluble fraction could not be separated clearly. Then, centrifugation was carried out with a batch-wise high speed centrifugal separator (10,000 G) to obtain an insoluble fraction and a soluble fraction. The temperature of solution during centrifugation was about 25° C.

Figure 2:
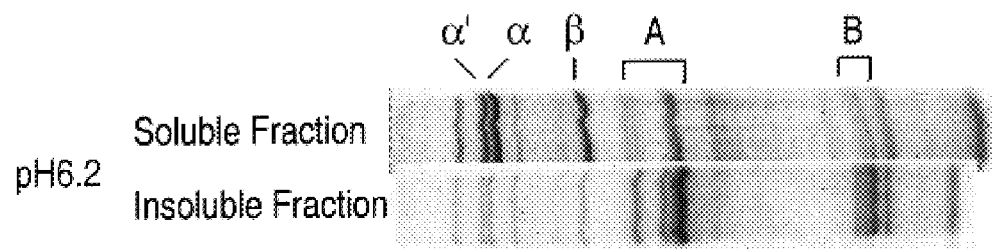

FIG. 2 shows a patter of SDS-polyacrylamide gel electrophoresis of the insoluble fraction and the soluble fraction of Comparative Example 1.

According to the same manner as that in Example 1, the amounts of 7S and 11S globulins present in the insoluble and soluble fractions were calculated. The results are shown in Table 2.

TABLE 2

|  | Soluble fraction | Insoluble fraction |
|---|---|---|
| Protein | 72.4 | 27.6 |
| 7S | 30.3 | 2.0 |
| 11S | 15.7 | 19.7 |
|  | Contamination rate of 11S | Contamination rate of 7S |
| Contamination rate | 21.7% | 7.2% |

In Example 1, the fractions treated by phytase were clearly separated with the centrifugal force as low as 2,000 G. However, in case no treatment with phytase was effected as in Comparative Example 1, 10,000 G was required for clear separation. Further, when the contamination rates of the soluble and insoluble fractions are compared, in Comparative Example 1, the contamination rate of 11S globulin in the soluble fraction is as high as 21.7% and the fractionation precision is not high. In contrast, in Example 1, the contamination rate of the fractions treated with phytase decrease to 1.9% and the fractionation precision is clearly improved.

These results show that treatment with phytase makes it possible to separate the soluble and insoluble fractions with an industrially applicable low centrifugal force, and is useful for a fractionation method with a lower contamination rate.

Test Example 1

Defatted-soybean milk extracted according to the same manner as that described in Example 1 was adjusted to pH 6.2 with hydrochloric acid and warmed to 40° C. To this solution was added phytase ("PHYTASE NOVO L" manufactured by NOVO) in an amount corresponding to 0.4 or 2 units based on the weight of protein, and enzyme treatment was carried out for 30 minutes. After the reaction, the mixture treated with the enzyme (phytic acid content: 1.83% or 0.87%/weight of protein) was centrifuged without changing pH at 6.2 by a batch-wise centrifugal separator (2,000 G) to obtain an insoluble fraction and a soluble fraction.

According to the same manner as that in Example 1, the amounts of 7S and 11S globulins present in the insoluble and soluble fractions of Test Example 1 were calculated. The results are shown in Tables 3 and 4.

TABLE 3

(phytase corresponding to 0.4 unit)

|  | Soluble fraction | Insoluble fraction |
|---|---|---|
| Protein | 68.2 | 31.8 |
| 7S | 27.6 | 1.5 |
| 11S | 10.9 | 24.7 |
|  | Contamination rate of 11S | Contamination rate of 7S |
| Contamination rate | 16.0% | 4.7% |

TABLE 4

(phytase corresponding to 2 units)

|  | Soluble fraction | Insoluble fraction |
|---|---|---|
| Protein | 57.5 | 42.5 |
| 7S | 25.9 | 2.7 |
| 11S | 1.5 | 31.2 |
|  | Contamination rate of 11S | Contamination rate of 7S |
| Contamination rate | 2.6% | 6.4% |

As seen from these results, in case of treatment with phytase for 30 minutes, as the amount of phytase to be added is higher, more improvement of fractionation is expected (provided that, when treatment with phytase is carried out for a longer period of time, a smaller amount of phytase can be used). The phytic acid content based on the weight of protein is 1.83% in case of treatment with phytase in the amount corresponding to 0.4 unit, and 0.87% in case of treatment with phytase in the amount corresponding to 2 units. When the reduction rate of phytic acid is calculated based on the phytic acid content before treatment with phytase (2.20%/weight of protein), it is 16.8% and 60.5%. Fractionation capability at 2,000 G is improved in either case. However, when 50% or more of the original phytic acid content is decomposed, fractionation precision is improved.

EXAMPLE 2

Defatted-soybean milk extracted according to the same manner as that described in Example 1 was adjusted to pH 5.9 or 6.4 with hydrochloric acid and warmed to 40° C. To this solution was added phytase ("PHYTASE NOVO L" manufactured by NOVO) in an amount corresponding to 8 units based on the weight of protein, and enzyme treatment was carried out for 30 minutes. After the reaction, the mixture treated with the enzyme (phytic acid content of each solution: 0.05%/weight of protein) was centrifuged without changing pH by a batch-wise centrifugal separator (3,000 G) to obtain an insoluble fraction and a soluble fraction.

According to the same manner as that in Example 1, the amounts of 7S and 11S globulins present in the insoluble and soluble fractions of Example 2 were calculated. The results are shown in Tables 5 and 6.

TABLE 5

(solution at pH 5.9)

|  | Soluble fraction | Insoluble fraction |
|---|---|---|
| Protein | 48.6 | 51.4 |
| 7S | 28.1 | 3.6 |
| 11S | 1.4 | 34.8 |
|  | Contamination rate of 11S | Contamination rate of 7S |
| Contamination rate | 2.9% | 7.0% |

TABLE 6

(solution at pH 6.4)

|  | Soluble fraction | Insoluble fraction |
|---|---|---|
| Protein | 60.0 | 40.0 |
| 7S | 28.6 | 2.1 |
| 11S | 4.1 | 30.6 |
|  | Contamination rate of 11S | Contamination rate of 7S |
| Contamination rate | 6.8% | 5.3% |

As seen from these results, pH at which centrifugation is carried out, i.e., fractionation pH ranges to some extent.

EXAMPLE 3

Defatted-soybean milk extracted according to the same manner as that described in Example 1 was adjusted to pH 4.0 or 7.0 with hydrochloric acid and warmed to 40° C. To this solution was added phytase ("PHYTASE NOVO L" manufactured by NOVO) in an amount corresponding to 8 units based on the weight of protein, and enzyme treatment was carried out for 30 minutes. After the reaction, the mixture of pH 4.0 (phytic acid content: 0.05%/weight of protein) was adjusted to pH 6.2 with sodium hydroxide, and the mixture of pH 7.0 (phytic acid content: 0.08%/weight of protein) was adjusted to pH 6.2 with hydrochloric acid. Then, each mixture was centrifuged by a batch-wise centrifugal separator (3,000 G) to obtain an insoluble fraction and a soluble fraction.

According to the same manner as that in Example 1, the amounts of 7S and 11S globulins present in the insoluble and soluble fractions of Example 3 were calculated. The results are shown in Tables 7 and 8.

TABLE 7

(phytase treatment at pH 4.0)

|  | Soluble fraction | Insoluble fraction |
|---|---|---|
| Protein | 39.8 | 60.2 |
| 7S | 24.0 | 5.5 |
| 11S | 1.0 | 34.5 |
|  | Contamination rate of 11S | Contamination rate of 7S |
| Contamination rate | 2.5% | 9.1% |

TABLE 8

(phytase treatment at pH 7.0)

|  | Soluble fraction | Insoluble fraction |
|---|---|---|
| Protein | 61.7 | 38.3 |
| 7S | 28.0 | 1.8 |
| 11S | 5.5 | 26.2 |
|  | Contamination rate of 11S | Contamination rate of7S |
| Contamination rate | 8.9% | 4.7% |

EXAMPLE 4

Defatted-soybean milk extracted according to the same manner as that described in Example 1 was adjusted to pH 4.5 with hydrochloric acid and centrifuged with a batch-wise centrifugal separator (2,000 G) to separate into an insoluble fraction (hereinafter referred to as acid precipitated curd) and a soluble fraction (whey). To the acid precipitated curd (so-called isolated soybean protein) was added water and the curd was thoroughly dispersed. The dispersion was adjusted to pH 6.2 with sodium hydroxide. To this solution (phytic acid content: 1.80%/weight of protein) was added phytase ("PHYTASE NOVO L" manufactured by NOVO) in an amount corresponding to 8 units based on the weight of protein, and enzyme treatment was carried out for 30 minutes. This mixture treated with the enzyme (phytic acid content: 0.05%/weight of protein, no substantial change in TCA solubilization degree) was centrifuged with a batch-wise centrifugal separator (2,000 G) to obtain an insoluble fraction and a soluble fraction. At this time, the insoluble fraction and the soluble fraction were clearly separated. The solution temperature upon centrifugation was about 30° C. To the insoluble fraction was added water (2 parts by weight) and neutralized with sodium hydroxide. The soluble fraction as such was neutralized with sodium hydroxide.

Each of them was sterilized at 140° C. for 15 seconds and spray-dried to obtain fractionated soybean proteins. These fractionated soybean proteins had better flavor and taste and better color in comparison with conventional isolated soybean protein.

According to the same manner as that in Example 1, the amounts of 7S and 11S globulins present in the insoluble and soluble fractions were calculated. The results are shown in Table 9.

TABLE 9

|  | Soluble fraction | Insoluble fraction |
| --- | --- | --- |
| Protein | 50.6 | 49.4 |
| 7S | 32.1 | 3.1 |
| 11S | 2.2 | 34.8 |
|  | Contamination rate of 11S | Contamination rate of 7S |
| Contamination rate | 4.3% | 6.3% |

As seen from these results, when an acid precipitated curd (so-called isolated soybean protein) is used as a soybean protein-containing solution to be used for the fractionation, separation can also be carried out in good precision.

Comparative Example 2

Defatted-soybean milk extracted according to the same manner as that described in Example 1 was boiled in a boiling water bath for 10 minutes. After cooling with water, the solution was adjusted to pH 6.2 with hydrochloric acid and warmed to 40° C. To this solution was added phytase ("PHYTASE NOVO L" manufactured by NOVO) in an amount corresponding to 8 units based on the weight of protein, and enzyme treatment was carried out for 30 minutes. After the reaction, the mixture treated with the enzyme (phytic acid content: 0.05%/weight of protein) was centrifuged without changing pH by a batch-wise centrifugal separator (2,000 G). However, an insoluble fraction and a soluble fraction could not be separated clearly. Then, the mixture was centrifuged with a batch-wise high speed centrifugal separator (10,000 G) to obtain an insoluble fraction and a soluble fraction. However, separation into the insoluble fraction and the soluble fraction was not clear and the recovery rate of the insoluble fraction was as low as only 11%. Thus, it was clear that the heat treatment before treatment with phytase adversely affected the fractionation.

What is claimed is:

1. A process for producing soybean 7S globulin and 11S globulin, which comprises:

treating a soybean protein-containing solution with an enzyme or an enzyme preparation having an activity of decomposing phytic acid, and adjusting the solution to a pH of 5.6 to 6.6, to thereby separate into a soluble fraction which is 7S globulin-rich fraction and an insoluble fraction which is an 11S globulin-rich fraction.

2. The process according to claim 1, wherein the soybean protein of the soybean protein-containing solution is not denatured.

3. The process according to claim 1, wherein the soybean protein-containing solution is treated with the enzyme or the enzyme preparation having the activity of decomposing phytic acid at a pH of 3.5 to 9.0 and a temperature of 20 to 70° C., for 5 minutes to 3 hours.

4. The process according to claim 1, further comprising:

concentrating the soluble or insoluble fraction to produce a concentrated fraction;

neutralizing the concentrated fraction to produce a neutralized fraction;

sterilizing with heat, the neutralized fraction to produce a sterilized fraction; and drying the sterilized fraction.

5. The process according to claim 2, wherein the soybean protein-containing solution is treated with the enzyme or the enzyme preparation having the activity of decomposing phytic acid at a pH of 3.5 to 9.0 and a temperature of 20 to 70° C., for 5 minutes to 3 hours.

6. The process according to claim 2, further comprising:

concentrating the soluble or insoluble fraction to produce a concentrated fraction;

neutralizing the concentrated fraction to produce a neutralized fraction;

sterilizing with heat, the neutralized fraction to produce a sterilized fraction; and drying the sterilized fraction.

7. The process according to claim 3, further comprising:

concentrating the soluble or insoluble fraction to produce a concentrated fraction;

neutralizing the concentrated fraction to produce a neutralized fraction;

sterilizing with heat, the neutralized fraction to produce a sterilized fraction; and drying the sterilized fraction.

* * * * *